United States Patent [19]
Kato et al.

[11] 4,269,893
[45] May 26, 1981

[54] RECORDING MATERIAL CONTAINING A NOVEL COLOR DEVELOPER

[75] Inventors: Hajime Kato; Masato Satomura, both of Fujinomiya; Kozo Sato, Minami-ashigara, all of Japan

[73] Assignee: Fuji Photo Film Co., Ltd., Minami-ashigara, Japan

[21] Appl. No.: 37,608

[22] Filed: May 10, 1979

[30] Foreign Application Priority Data

May 12, 1978 [JP] Japan ................................. 53/56214

[51] Int. Cl.³ ......................... B41L 1/20; B41M 5/16; B41M 5/22
[52] U.S. Cl. .................................. 428/341; 252/316; 282/27.5; 427/150; 427/161; 428/206; 428/207; 428/307; 428/914; 428/342; 428/341
[58] Field of Search ............... 282/27.5; 428/411, 914, 428/307, 913, 340, 341, 207, 206; 252/316

[56] References Cited

U.S. PATENT DOCUMENTS

| | | | |
|---|---|---|---|
| 3,418,250 | 12/1968 | Vassiliades | 252/316 |
| 3,432,327 | 3/1969 | Kan et al. | 282/27.5 |
| 3,864,146 | 2/1975 | Oda et al. | 282/27.5 |
| 3,871,900 | 3/1975 | Hayashi et al. | 282/27.5 |
| 3,900,215 | 8/1975 | Kato et al. | 282/27.5 |
| 3,996,405 | 12/1976 | Porter | 428/307 |
| 4,076,887 | 2/1978 | Tsuji et al. | 282/27.5 X |

*Primary Examiner*—Thomas J. Herbert, Jr.
*Attorney, Agent, or Firm*—Sughrue, Rothwell, Mion, Zinn and Macpeak

[57] ABSTRACT

A recording material in which a particular salicylic acid derivative is employed as a color developer, which derivative is a reaction product of a styrene dimer, an alkylstyrene dimer or the halogen substituted products thereof which material exhibits improved water resistivity, keeping stability and workability, does not produce color contamination when dipped in water and can exhibit its color-developing ability without special treatment.

11 Claims, No Drawings

RECORDING MATERIAL CONTAINING A NOVEL COLOR DEVELOPER

BACKGROUND OF THE INVENTION

1. Field of the Invention

The present invention relates to a recording material and particularly, to a recording material in which a novel color developer is employed.

2. Description of the Prior Art

Recording materials utilizing substantially colorless color formers which can produce color upon contact with acidic substances (a color developer) are well known. Specific examples of such recording materials include; for instance, pressure sensitive copying paper, heat sensitive recording paper, electro thermo-recording paper and so on, and they are described in detail in U.S. Pat. Nos. 2,712,507; 2,730,456; 2,730,457; 3,418,250; 3,432,327; 3,981,821; 3,993,831; 3,996,156; 3,996,405 and 4,000,087; etc. In these recording materials, clay minerals such as acid clay, bentonite, kaolin or the like; isopropenylphenol dimer; phenol-formaldehyde novolak resins; metal-processed novolak resins; di-tert-butylsalicylic acid; etc. are used as color developers. As a color former, compounds which are usually substantially colorless and have in their skeleton a lactone, a lactam, a sultone, a spiropyran, an ester, an amido or like structures, which undergoes ring opening or bond fission upon contact with a color developer, have been employed. Specific examples of such color formers include Crystal Violet lactone, benzyl leuco Methylene Blue, Malachite Green lactone, Rhodamine B lactam, 1,3,3-trimethyl-6'-ethyl-8'-butoxyindolinobenzospiropyran and the like. These color formers may be used in combination depending upon the end use.

When the above described color developers are employed in a recording material, the recording material lacks water resistivity, has low keeping stability, has a high melting point and consequently low workability, color contamination appears when it is dipped in water, special treatment is required to enable the color developer to fully exhibit its color developing ability and others. For instance, when a salicylic acid derivative such as 3,5-di-α-methylbenzylsalicylic acid or the metal salt thereof is employed as a color developer, it is known that it does not exhibit its full color developing ability unless it is subjected to a sand grinding mill treatment. Overcoming these disadvantages is an important subject of this art.

SUMMARY OF THE INVENTION

Therefore, a principal object of the present invention is to provide a recording material which possesses high resistivity to water, high keeping stability, good workability, markedly reduced color contamination when dipped in water, and which is capable of exhibiting its full color developing ability without special treatments.

The above-described object is attained by employing, as a color developer, a reaction product of salicylic acid and a styrene dimer, an alkylstyrene dimer or the halogen substituted products thereof at the benzene nucleus of the salicylic acid.

DETAILED DESCRIPTION OF THE INVENTION

In the present invention, preferable examples of alkylstyrenes include styrenes wherein the benzene nucleus or at least one α-position is substituted with an alkyl group having about 1 to 5 carbon atoms, (e.g., α-alkylstyrenes such as α-methylstyrene, α-ethylstyrene, etc.; vinyltoluene and more particularly a mixture of ortho-, meta- and para- vinyltoluenes; isopropyltoluene; isopropenyl chlorobenzene; ethylstyrene and more particularly a mixture of ortho-, meta- and para-ethylstyrenes; t-butylstyrene and more particularly a mixture of ortho-, meta- and para-t-butylstyrenes; etc.). The above-described alkylstyrenes are particularly effective when employed in admixture.

In the present invention, the dimer may be represented by, for example, the following formulae (I) and (II):

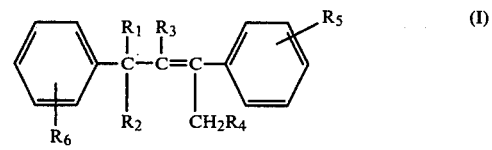

or

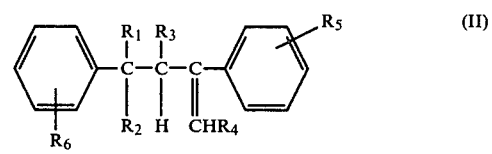

wherein $R_1$ to $R_4$ each represents a hydrogen atom or an alkyl group, and $R_5$ and $R_6$ each represents a hydrogen atom, an alkyl group or a halogen atom. The alkyl group may be straight chain, branched chain or cyclic and contain 1 to 5 carbon atoms. The halogen atom may be fluorine, chlorine, bromine or iodine.

Specific examples of such dimers are illustrated below. These dimers are provided for illustration purposes only and are not intended to limit the scope of the present invention.

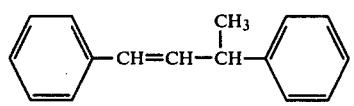

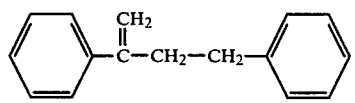

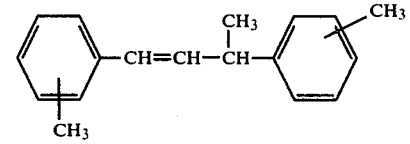

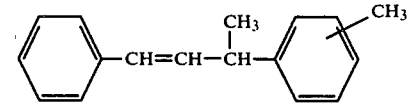

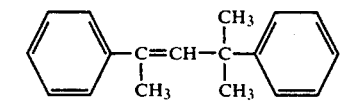

-continued

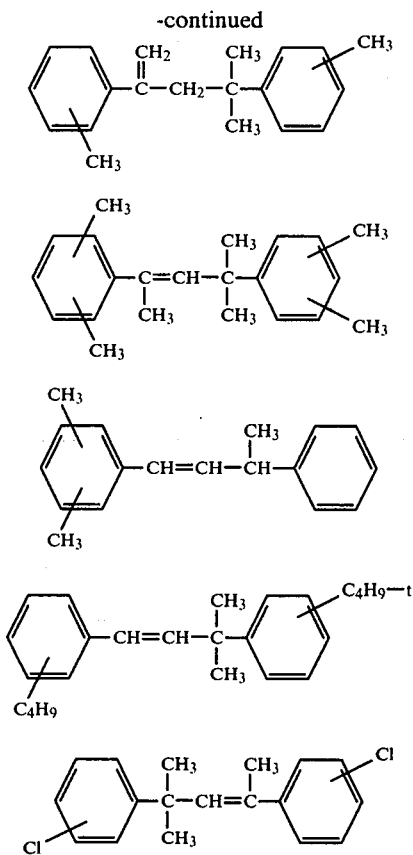

These dimers may be used in combination. Sometimes the dimers used in the present invention will contain a small amount of cyclized dimer as an impurity.

The salicylic acid is substituted by the dimer at at least one of the 3- and the 5-positions. In the present invention, preferred examples of the reaction product of a salicylic acid and a styrene dimer, an alkyl styrene dimer or a halogen substituted styrene or alkyl styrene dimer may be represented by the following formula (III):

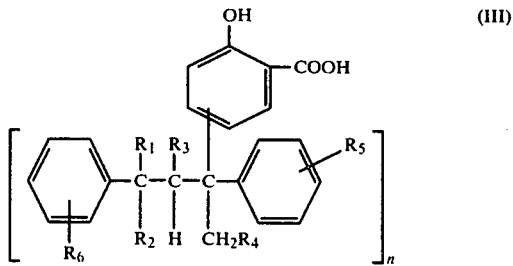

wherein $R_1$ to $R_4$ each represents a hydrogen atom or an alkyl group, $R_5$ and $R_6$ represent a hydrogen atom, an alkyl group or a halogen atom and n is 1 or 2. When n=2 the salicylic acid is disubstituted, e.g., at the 3- and 5-positions.

The compounds which are substituted at the 5-positions are easy to handle and useful.

The salicylic acid derivatives of the present invention substituted with a styrene dimer or an alkylstyrene dimer are much more effective when used in the form of a metal salt. Specific examples of metals which may form the salts together with the salicylic acid derivatives may include divalent and trivalent metals such as zinc, aluminium, tin, barium, calcium, magnesium, nickel, cobalt, strontium and so on. These metal salts also can be used in combination. Preferable metal salts are white and the zinc salt and aluminium salt are particularly preferred.

As mentioned above these compounds can be employed in combinations of two or more. Accordingly, the metal salt used may contain a mixture of salicylic acid derivatives; for example, taking the case of zinc salt, it may be a coordination compound in which the zinc ion coordinates with two identical salicylic acid derivatives of a first type, a compound in which the zinc ion coordinates with two identical salicylic acid derivatives of a second type, a coordination compound in which the zinc ion coordinates with different salicylic acid derivatives and the like.

The salicylic acid derivatives substituted with the particular dimers illustrated hereinbefore have various advantages of (i) lower solubility in water compared with a salicylic acid which is substituted with an alkylstyrene monomer; (ii) improved solubility in oils and particularly in aromatic oils; (iii) high solubility in color former dissolving oils and a color developing ability capable of being easily brought into full play; (iv) improved higher developing speed; (v) improved keeping stability due to the difficulty in hydrolysis caused by moisture in air; and others.

In obtaining a recording material exhibiting the above-described advantages, the use of the derivatives of salicylic acid substituted with a dimer of styrene, an alkylstyrene or a halostyrene is of vital importance. In case of a derivative of salicylic acid substituted with styrene monomer or the like, the recording material is scarcely fit for practical use due to the color developer's solubility to water and low solubility in oils.

The preparation of the salicyclic acid derivatives of the present invention can be carried out by: (1) a method, in which a phenol is substituted with an aralkyl group such as a styrene, alkylstyrene, halostyrene dimer or the like and the product is subjected to a Kolbe-Schmidt reaction; or (2) aralkylation of salicylic acid with the dimer; and other methods.

The styrene dimers used in the present invention may be cyclic saturated dimers or linear unsaturated dimers. The unsaturated dimer is synthesized by dimerizing the styrenes in a nonpolar solvent such as benzene, toluene, etc., using as a catalyst a strong acid such as sulfuric acid, sulfonic acid, perchloric acid and the like or by dimerizing the styrenes with the solid acid catalyst such as active clay at a temperature of room temperature to 150° C. In many cases, reaction controlling agents such as ketones, aldehydes, esters, alcohols, etc., may be added.

An addition reaction of the styrene dimer and the phenol can be carried out easily in the presence or absence of a solvent in the presence of an acidic catalyst such as sulfuric acid, sulfonic acid, phosphoric acid, active clay at a temperature of room temperature at 150° C. Further, the styrene dimer may be added dropwise to control the formation of di-substituted by products.

The Kolbe reaction is generally carried out by producing the sodium salt of the phenol from sodium hydroxide, azeotropic distillation of the water formed together with toluene and xylene, and then placing the reaction product in the autoclave followed by reacting at the temperature of 100° to 200° C. while introducing carbonic acid gas at a pressure of 10 to 100 Kg/cm². On a small scale, the simple Marasse method, e.g., the method of reacting the phenol with the calcium carbonate anhydride in the absence of solvent or in the presence of the dimethylformamide solvent, is carried out.

The color developer of the present invention can also be employed in the form of an ink. Moreover, on the occasion that the salicylic acid derivatives of the present invention are used in a form of a metal salt, the derivative may be first converted to the metal salt and then coated; or the metal salt may be formed in the process of coating-drying of the derivative; or the derivative may be transformed into the metal salt upon being supplied with a metal upon recording. An embodiment of the last case includes specifically the process of adding the metal salt of an acid having weaker acidity than the salicylic acid to a capsule oil or to a color former containing layer in advance, and causing salt formation to occur upon pressure transfer.

The color formers capable of coloring upon contact with the color developer of the present invention include compounds exhibiting absorption in the visible region upon the contact with the organic acids. Representative examples of such color formers include substantially colorless compounds having in their partial skeleton a lactone, a lactam, a sultone, a spiropyran, an ester or an amido structure. Specifically, there are triarylmethane compounds, diphenylmethane compounds, xanthene compounds, thiazine compounds, spiropyran compounds and the like. Typical examples of them include Crystal Violet lactone, benzoyl leuco methylene blue, Malachite Green Lactone, p-nitrobenzoyl leuco methylene blue, 3,-dialkylamino-7-dialkylaminofluoran, 3-methyl-2,2'-spirobi(benzo-f-chromene), 3,3-bis(p-dimethylaminophenyl)phthalide, 3-(p-dimethylaminophenyl)-3-(1,2-dimethylindole-3-yl)phthalide, 3-(p-dimethylaminophenyl)-3-(2-methylindole-3-yl)phthalide, 3-(p-dimethylaminophenyl)-3-(2-phenylindole-3-yl)phthalide, 3,3-bis(1,2-dimethylindole-3-yl)-5-dimethylaminophthalide, 3,3-bis-(1,2-dimethylindole-3-yl)-6-dimethylaminophthalide, 3,3-bis-(9-ethylcarbazole-3-yl)-5-dimethylaminophthalide, 3,3-bis-(2-phenylindole-3-yl)-5-dimethylaminophthalide, 3-p-dimethylaminophenyl-3-(1-methylpyrrole-2-yl)-6-dimethylaminophthalide, 4,4'-bis-dimethylaminobenzhydrin benzyl ether, N-halophenyl leuco Auramine, N-2,4,5-trichlorophenyl leuco Auramine, Rhodamine-B-anilinolactam, Rhodamine-(p-nitroanilino)lactam, Rhodamine-B-(p-chloroanilino)lactam, 3-dimethylamino-6-methoxyfluoran, 3-diethylamino-7-methoxyfluoran, 3-diethylamino-7-chloro-6-methylfluoran, 3-diethylamino-6-methyl-7-anilinofluoran, 3-diethylamino-7-(acetylmethylamino)fluoran, 3-diethylamino-7-(dibenzylamino)fluoran, 3-diethylamino-7-(methylbenzylamino)fluoran, 3-diethylamino-7-(chloroethylmethylamino)fluoran, 3-diethylamino-7-(diethylamino)fluoran, 3-methyl-spiro-dinaphthopyran, 3-ethyl-spiro-dinaphthopyran, 3,3'-dichloro-spiro-dinaphthopyran, 3-benzyl-spiro-dinaphthopyran, 3-methyl-naphtho-(3-methoxybenzo)-spiropyran, 3-propyl-spiro-dibenzodipyran and so. These color formers may be used in combination.

Solvents suitable for dissolving these color formers for encapsulation are selected from those which can dissolve the color former in a concentration of 0.1 wt.% or more and particularly, those which can dissolve Crystal Violet lactone in a concentration of about 0.5 wt.% or more. Herein the term "the concentration" means the amount of a single or a plurality of color formers dissolved at a temperature of 23° C. Solvents which do not give rise to precipitation of color former(s) when the solution of color former(s) is allowed to stand for three days are particularly favorable.

Under certain circumstances, there may be color formers which are difficult to be dissolved in a certain solvent as long as they are used individually, but when used in a combination they become soluble in that solvent. Accordingly, an optimum combination of color formers can be determined based on trial and error.

Specifically, such solvents include chlorine containing compounds and aromatic compounds. For example, chlorinated paraffins (having 10 to about 20 carbon atoms and a degree of chlorination ranging from about 15% to 60% or so), alkyl- or aralkyl-benzenes or naphthalenes the alkyl moiety of which contains about 1 to 5 carbon atoms (e.g., triphenylmethane, diphenyltolylmethane, xylylphenylethane, benzylxylene, $\alpha$-methylbenzyltoluene, diisopropylnaphthalene, isobutylbiphenyl, tetrahydronaphthalene, hydrogenated terphenyl, di-$\alpha$-methylbenzyl, xylene, tert-butyl-diphenyl ether, hydrogenated styrene dimer, etc.) are suitable.

Assistant solvents such as paraffins, alkenes, ethers, esters, fatty acids or the zinc salts thereof, and the like, which have a boiling point of about 80° C. to 250° C. also can be added to the above-described solvents in a proportion of about 50 wt.% or less.

The color formers dissolved in one or more of the solvents described above are subjected to a microencapsulation treatment. As the examples of microencapsulation methods, mention may be made of coacervation as disclosed in U.S. Pat. Nos. 2,800,457 and 2,800,458; interfacial polymerization as disclosed in British Pat. No. 990,443 and U.S. Pat. No. 3,287,154; polymer separation as disclosed in U.S. Pat. Nos. 3,418,250, 3,660,304 and 4,011,140 and Japanese Patent Publication No. 23,165/72 a method based on polymerization of a reactant which separates out of the oil droplets, as disclosed in U.S. Pat. Nos. 3,726,804 and 3,796,669, etc.

The thus obtained color former-containing capsules are coated on the same surface or the opposite surface of a support containing the color developer coated layer, or the color former-containing capsules and the color developer are coated on independent supports which are arranged with color former and color developer facing one another resulting in the preparation of a recording material.

Coating techniques and the use of various kinds of additives such as a binder, an antioxidant, a smudge inhibitor, a surface active agent, etc., applicable on the occasion of capsule layer-making are well-known and described in U.S. Pat. Nos. 2,711,375, 3,625,736, 3,836,383 and 3,846,331, British Patent No. 1,232,347, Japanese Patent Publications Nos. 44,012/75, 50,112/75, 127,718/75 and 30,615/75, etc.

The color former is used in a coated amount of 0.05 g/m² to 0.5 g/m² and particularly, it is convenient to use the color former in a coated amount of 0.08 g/m² to 0.3 g/m². On the other hand, the color developer is usually employed in a coated amount of 0.1 g/m² to 3 g/m², preferably 0.2 to 1 g/m².

In addition, on the occasion of providing the color developer layer the combined use of the above-described salicylic acid derivative or the polyvalent metal salt thereof and a metallic compound; preferably, the oxide, hydroxide, carbonate, acetate or phosphate of a polyvalent metal of zinc, aluminium, barium, calcium, silicon or the like, and talc, clay, active clay or the like, in a mixing ratio of the amount of the salicylic acid derivative to that of the metallic compound ranging from about 10:1 to about 10:300 by weight and preferably from about 10:50 to about 10:200 is advantageous because the color developing ability can be improved due to such a combined use through such a metallic compound alone does not have any color developing ability. These compounds are coated on a paper support as a solution or dispersion obtained by dissolving or dispersing them in an organic solvent or water. At the time of dissolution or dispersal, these compounds are finely pulverized in advance using general grinding techniques under a wet or a dry condition.

Furthermore, a latex or a water soluble polymer; such as carboxy denatured styrene-butadiene copolymer, butadiene-butyl acrylate-styrene-maleic acid copolymer, vinyl acetate-styrene-methylmethacrylate copolymer, isoprene-maleic acid-acrylonitrile copolymer, petroleum resin, oxidized starch, polyvinyl alcohol, methyl cellulose or the like, can be optionally used in a proportion of about 10 to 25 wt.% based on the total weight of solid component contained in the color developing layer. To such a solution or a dispersion, a dispersant, stabilizer and the like may be added. The color developer layer is usually employed at a coverage of about 0.2 to 12 g/m².

These layers are coated on a support using a coating technique described in the above-described patent specifications; for instance by dip coating, air knife coating, blade coating, roller bead coating, curtain coating, gravure coating or like coating techniques. As the support, sized paper, a film base or the like can be employed.

In general, the color developer layer should have a smooth surface. Therefore, it is usually pressed once by calendering or like treatment in order to smoothen its surface.

The present invention will now be illustrated in greater detail by reference to the following examples. Therein, a microcapsule dispersion was prepared according to the process described in the Example 2 of U.S. Pat. No. 3,956,172.

To the microcapsule dispersion, starch grains (having a size of 15μ) and cellulose flocks in a mixing ratio of 2:1 were added in an amount corresponding to 1.3 times that of the solid components contained in the dispersion. The resulting dispersion was coated on paper having a weight of 40 g at a coverage of 0.093 g/m² of color former per square meter.

SYNTHESIS EXAMPLE 1

2 g of a p-toluenesulfonic acid was added to 47 g (0.5 mole) of phenol, and they were heated at a temperature of 130° to 140° C. To the resulting solution, 20.8 g (0.1 mole) of styrene dimer, prepared in accordance with British Patent No. 1,530,430 was added dropwise over 2 hours. After the conclusion of dropwise addition, stirring was continued for 30 minutes at the same temperature. To the reaction product, 100 ml of water and sodium hydrogen-carbonate were added and then, excess phenol was removed therefrom by steam distillation. Thus, a pale yellow oily residue was obtained which was extracted with benzene, washed with water and dried. Then, the benzene was removed therefrom and 31 g of a styrene dimer-phenol addition product, 1,3-diphenylbutyl-phenol (a pale yellow viscous liquid) was obtained.

The thus obtained adduct and 100 g of anhydrous potassium carbonate were placed in a 1 liter autoclave and thereinto, carbon dioxide gas was introduced at a pressure of 40 Kg/cm². The mixture was shaken for 5 hours at 180° C. To the product obtained, 200 ml of water and 200 ml of benzene was added under ordinary pressure, and the product was dissolved therein by application of heat. The organic phase which separated out was removed and shaken together with a dilute hydrochloric acid solution to convert the potassium salt into the free acid. The product was washed with water, dried and then, distilled to remove benzene. Thus, 34 g of crude product of 1,3-diphenylbutylsalicylic acid was obtained. It was light brown viscous liquid, and the yield was 98%.

A 17.3 g portion of the crude product obtained (0.05 mole) was dissolved in an aqueous solution of sodium hydroxide (containing 2 g of NaOH), and the resulting solution was added to a solution prepared by dissolving 17.4 g of crystalline zinc sulfate (0.06 mole) in 500 ml of water, and stirring was continued for 1 hour at a room temperature. A white precipitate precipitated. The precipitate was filtered off, washed with water and dried to obtain zinc (1,3-diphenylbutyl)salicylic (consisting of 3- and 5-substituted salicylic.

SYNTHESIS EXAMPLE 2

33.0 g (0.1 mole) of p-(1,3-dimethyl-1,3-diphenylbutyl)phenol and 100 g of anhydrous potassium carbonate were placed in an autoclave and thereto, carbon dioxide gas was introduced at a pressure of 40 Kg/cm². Then, the mixture was shaken at 180° C. for 5 hours. After cooling to room temperature, the pressure in the autoclave was returned to atmospheric pressure and then, 200 ml of water and 400 ml of benzene were added to the reaction product in the autoclave, followed by heating them in order to dissolve the reaction product in these solvents. The organic phase separated out was taken out of the autoclave and shaken with a dilute hydrochloric acid solution to convert the potassium salt into the corresponding free acid. Then, it was washed with water, dried and then, concentrated in order to remove the benzene. Thus, white needle crystal was separated out. The crystal was filtered off to obtain 31.8 g of 5-(1,3-dimethyl-1,3-diphenylbutyl)salicylic acid (yield: 85%, mp: 153°–155° C.).

A 18.7 g portion of the thus obtained acid (0.05 mole) was added to a solution of 2 g of sodium hydroxide in 100 ml of water, and dissolved therein by application of heat. The resulting solution was added to an aqueous solution of zinc sulfate (containing 17.4 g (0.06 mole) of crystalline zinc sulfate) with vigorous stirring. After stirring was continued for an additional hour at a room temperature, a white precipitate of zinc salt separated out and was filtered off, and washed with water. The product could be obtained almost quantitatively.

SYNTHESIS EXAMPLE 3

The zinc salicylate of the following chemical structure was prepared as follows:

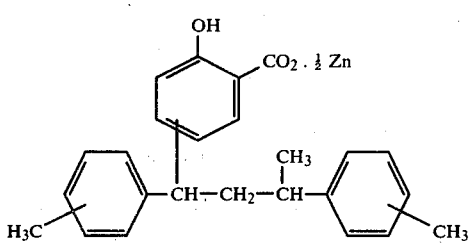

(1,3-Dibutyl)phenol was prepared in the same manner as in Synthesis Example 1 except that 23.6 g (0.1 mole) of vinyltoluene dimer in the place of styrene dimer was used. Further, the resulting product was subjected to a Kolbe reaction under the same condition as in Synthesis Example 1 and the reaction product was converted to the zinc salt to obtain the zinc (1,3-ditolylbutyl) salicylate.

SYNTHESIS EXAMPLE 4

The zinc salicylate of the following chemical formula was prepared as follows:

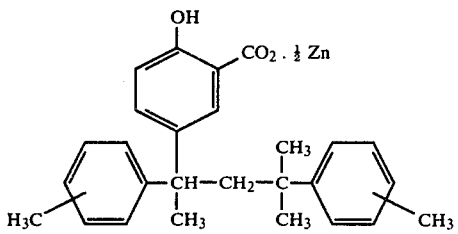

The addition reaction and the Kolbe reaction were conducted in the same manner as in Synthesis Example 1 except that 26.4 g (0.1 mole) of isopropenyltoluene was used in place of the styrene dimer used in Synthesis Example 1 and the reaction product was converted to the zinc salt to obtain the zinc (1,3-dimethyl-1,3-ditolyl-butyl)salicylate.

These zinc salicylates all exhibit an ultraviolet absorption maximum in the neighborhood of about 310–320 m$\mu$ when measured in ethanol, and only slightly soluble in water.

EXAMPLE 1

To the mixture of 40 parts of talc, 1 part of sodium oligostyrenesulfonate (Oligo Z, trade name of Tomoegawa Paper Mfg. Co., Ltd.), 26 parts of zinc oxide grains having a diameter of 1$\mu$, 50 parts of aluminium hydroxide and 7.5 parts of the metal salt obtained in the above-described Synthesis Example 1, 150 ml of water was added and then, it was ground for 20 minutes using an attriter to obtain grains having an average diameter of about 4$\mu$. To the thus obtained grains, 30% aqueous solution of the mixture consisting of oxidized starch, polyvinyl alcohol and carboxy denatured styrenebutadiene latex in a mixing ratio of 3:5.5:9 was added in an amount corresponding to the concentration of 15% to the weight of the above-described solid component. The resulting dispersion was applied to starch sized (1.5 g/m$^2$) paper at a coverage of 0.43 g/m$^2$ of the metal salt prepared in Synthesis Example 1.

The thus obtained color developer sheet and the capsule sheet were allowed to come into face-to-face contact, and pressure was applied thereto using typewriter. Very clearly colored images of high density could be obtained. Images obtained had sufficient stability and water resistivity.

In addition, the compound of the present invention exhibits very high compatibility with resins when used in a form of mixture with other resins, as disclosed in U.S. Pat. No. 3,924,027.

Furthermore, the compound of the present invention can provide clear coloration without receiving any special treatments as disclosed in Japanese Patent Application (OPI) No. 102413/75 and without receiving conventional ripening treatments.

EXAMPLE 2

Color developer coated paper was prepared in the same manner as in Example 1 except that acid clay instead of talc, sodium hexametaphosphate instead of sodium oligostyrenesulfonate, and further the zinc salicylate obtained in Synthesis Example 2 instead of that obtained in Synthesis Example 1 were employed. Therein, the coverage of the compound obtained in Synthesis Example 2 was adjusted to 0.26 g/m$^2$ instead of the coverage in Example 1. The thus obtained color developer coated paper was subjected to the same treatments as in Example 1, and very clear stable images could be quickly produced.

EXAMPLE 3

Clear images could be obtained in the same manner as in Example 2 except that the mixture of the zinc salicylate prepared in synthesis Example 3 and the other zinc salicylate prepared in Synthesis Example 4 (in a mixing ratio of 1:1 by weight) was employed instead of the compound prepared in Synthesis Example 2. In addition, when the color developer coated surface and the capsule coated surface were allowed to come into contact with each other and dipped in water for 2 minutes, followed by air-drying, color contamination was hardly observed therein.

EXAMPLE 4

Color developer coated paper was prepared in the same manner as in Example 2 except that calcium carbonate instead of aluminium hydroxide, and the compound obtained in Synthesis Example 4 instead of the compound obtained in Synthesis Example 2 were employed. In this case also, clear images of high density could be obtained.

While the invention has been described in detail and with reference to specific embodiments thereof, it will be apparent to one skilled in the art that various changes and modifications can be made therein without departing from the spirit and scope thereof.

What is claimed is:

1. In a recording material in which images are formed by the reaction of a substantially colorless color former with a color developer, the improvement which comprises said color developer comprising the reaction product of salicyclic acid and a styrene dimer or a metal salt thereof, wherein said reaction product is represented by the following general formula:

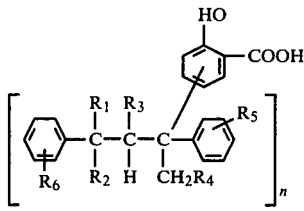

wherein $R_1$ to $R_6$ each represents a hydrogen atom or an alkyl group having 1 to 5 carbon atoms, $R_5$ and $R_6$ represents a hydrogen atom or an alkyl group having 1 to 5 carbon atoms or halogen atom and n is 1 or 2.

2. The recording material of claim 1, wherein said color developer is coated on a support in an amount of 0.1 g/m² to 3.0 g/m².

3. The recording material of claim 1, wherein said salicylic acid is substituted with said dimer at at least one of the 3-position and the 5-position.

4. The recording material of claim 3, wherein said color developer additionally contains an oxide, hydroxide, carbonate, acetate or phosphate of a polyvalent metal salt selected from the group consisting of zinc, aluminium, barium, silicon and calcium.

5. The recording material of claim 3, wherein said color developer additionally contains talc, clay, or active clay.

6. The recording material of claim 3, wherein said color developer is coated on said support in a latex or water soluble polymer binder.

7. The recording material of claim 1, wherein said color developer is a metal salt of said reaction product.

8. The recording material of claim 7, wherein said metal forming said metal salt is a divalent or trivalent metal.

9. The recording material of claim 7, wherein said metal forming said metal salt is selected from the group consisting of zinc, aluminium, tin, barium, calcium, magnesium, nickel, cobalt and strontium.

10. The recording material of claim 7, wherein said metal forming said metal salt is zinc or aluminium.

11. The recording material of claim 7, wherein said salt is a metal complex salt.

* * * * *